(12) United States Patent
Parton

(10) Patent No.: US 9,908,836 B2
(45) Date of Patent: Mar. 6, 2018

(54) PROCESS FOR THE ISOLATION OF LEVULINIC ACID AND FORMIC ACID

(71) Applicant: DSM IP ASSETS B.V., Heerlen (NL)

(72) Inventor: Rudy Francois Maria Jozef Parton, Echt (NL)

(73) Assignee: Georgia-Pacific LLC, Atlanta, GA (US)

( * ) Notice: Subject to any disclaimer, the term of this patent is extended or adjusted under 35 U.S.C. 154(b) by 299 days.

(21) Appl. No.: 14/648,437

(22) PCT Filed: Dec. 9, 2013

(86) PCT No.: PCT/EP2013/075961
§ 371 (c)(1),
(2) Date: May 29, 2015

(87) PCT Pub. No.: WO2014/087015
PCT Pub. Date: Jun. 12, 2014

(65) Prior Publication Data
US 2015/0299087 A1  Oct. 22, 2015

Related U.S. Application Data

(60) Provisional application No. 61/734,523, filed on Dec. 7, 2012.

(30) Foreign Application Priority Data

Dec. 7, 2012  (EP) .................................... 12196080
May 16, 2013  (EP) .................................... 13168025

(51) Int. Cl.
| | |
|---|---|
| C07C 51/47 | (2006.01) |
| C07C 51/48 | (2006.01) |
| C07C 51/42 | (2006.01) |
| B01D 3/40 | (2006.01) |
| C07C 51/44 | (2006.01) |
| C07C 59/185 | (2006.01) |

(52) U.S. Cl.
CPC ................ *C07C 51/47* (2013.01); *B01D 3/40* (2013.01); *C07C 51/42* (2013.01); *C07C 51/44* (2013.01); *C07C 51/48* (2013.01); *C07C 59/185* (2013.01)

(58) Field of Classification Search
CPC ........... B01D 3/40; C07C 51/42; C07C 51/47; C07C 51/48
See application file for complete search history.

(56) References Cited

U.S. PATENT DOCUMENTS

| 2,257,389 A | 9/1941 | Macallum |
| 2,648,704 A | 8/1953 | Ogawa et al. |
| 2,840,605 A | 6/1958 | Leonard |
| 7,520,905 B1 | 4/2009 | Lightner |
| 2010/0324310 A1 | 12/2010 | Dumesic et al. |
| 2012/0302766 A1 | 11/2012 | Dumesic et al. |
| 2014/0128634 A1* | 5/2014 | Mullen .................. C07C 51/00 562/577 |

FOREIGN PATENT DOCUMENTS

| FR | 1105538 A | 12/1955 |
| GB | 583533 A | 12/1946 |
| WO | 2010030617 A1 | 3/2010 |

OTHER PUBLICATIONS

International Search Report from corresponding PCT/EP2013/075961, dated Mar. 3, 2014.

* cited by examiner

*Primary Examiner* — Renee Robinson
(74) *Attorney, Agent, or Firm* — Ram W. Sabnis

(57) ABSTRACT

The invention provides a process for the isolation of levulinic acid and formic acid from a composition comprising formic acid and levulinic acid, said process comprising a solid-liquid separation step, a vapor removal step, and a solvent-solvent extraction step, wherein a vapor condensate vapor and/or an aqueous phase from the solvent extraction is used to wash the solid fraction. Washing with vapor condensate results in higher levulinic acid yields (higher levulinic acid recovery) as compared to washing with normal water. Washing with aqueous phase results in a less compressible filter cake. Washing first with aqueous phase and subsequently with condensate results in even higher levulinic acid yields. The process is suitable for isolating levulinic acid and formic acid from compositions made by acid hydrolysis of a lignocellulosic biomass, and also from compositions made by acid hydrolysis of sugars such as glucose and fructose.

20 Claims, No Drawings

PROCESS FOR THE ISOLATION OF LEVULINIC ACID AND FORMIC ACID

CROSS REFERENCE TO RELATED APPLICATIONS

This application is a § 371 National Stage Application of PCT/EP2013/075961, filed 9 Dec. 2013, which claims priority to EP 12196080.1, filed 7 Dec. 2012, U.S. 61/734,523, filed 7 Dec. 2012 and EP 13168025.8, filed 16 May 2013.

BACKGROUND

Field of the Invention

The present invention relates to a process for the isolation of levulinic acid and formic acid.

Description of Related Art

Levulinic acid is a starting molecule for the synthesis of esters known as fuel additive and is known to be useful as plasticisers and solvents. Levulinic acid can be used to synthesize methyl tetrahydrofuran (MTHF) or can be used as a solvent. Other applications of levulinic acid are for example the synthesis of delta-amino levulinic acid used as herbicides and pesticides, diphenolic acid used to synthesize polycarbonates and succinic acid used to make polyesters. Levulinic acid can also be used to produce gamma valerolactone (5-methylbutyrolactone), which in turn can be used for production of adipic acid (1,6-hexanedioic acid).

Formic acid is used as a preservative and antibacterial agent in livestock feed, in the production of leather, and in dyeing and finishing of textile. It is also used as coagulant in the production of rubber as well as cleaning agent assistant and potential future fuel for fuel cells.

US2010/0324310 relates to the production of both formic acid and levulinic acid. A problem of the process of US2010/0324310 is that the yield, particular of levulinic acid, is insufficient.

SUMMARY

The invention provides an improved process for the isolation of levulinic acid and formic acid from a composition comprising formic acid and levulinic acid, said process comprising a solid-liquid separation step, a vapor removal step, and a solvent-solvent extraction step, wherein a vapor condensate and/or an aqueous phase from the solvent extraction is used to wash the solid fraction. Washing with a vapor condensate results in higher levulinic acid yields (higher levulinic acid recovery) as compared to washing with normal water. Washing with aqueous phase results in a less compressible filter cake. Washing first with aqueous phase and subsequently with vapor condensate results in even higher levulinic acid yields. The process is suitable for isolating levulinic acid and formic acid from compositions made by acid hydrolysis of a lignocellulosic biomass, and also from compositions made by acid hydrolysis of sugar such as glucose and fructose.

DETAILED DESCRIPTION OF A PREFERRED EMBODIMENT

The invention provides a process for the isolation of levulinic acid and formic acid from a composition comprising formic acid and levulinic acid, said process comprising a solid-liquid separation step, a vapor removal step, and a solvent-solvent extraction step, wherein a vapor condensate and/or an aqueous phase from the solvent-solvent extraction step is used to wash a solid fraction obtained by the solid-liquid separation step.

The solid-liquid separation step and the vapor removal step can be done in any order. The order of the solid-liquid separation step and the vapor removal step has no effect of the washing with the condensate and/or the aqueous phase.

In one embodiment, the process is carried out as follows:
subjecting a composition comprising formic acid and levulinic acid to a solid-liquid separation to yield a solid fraction and a liquid fraction and recovering the liquid fraction;
concentrating said liquid fraction by a vapor removal step step to yield a concentrate and a vapor, and condensing said vapor to a condensate;
subjecting the concentrate to solvent-solvent extraction by adding an organic solvent to yield an organic phase comprising levulinic acid and/or formic acid and an aqueous phase and recovering the organic phase; and
isolating the levulinic acid and/or the formic acid from the organic phase e.g. by distillation,
characterized in that the condensate and/or the aqueous phase is used to wash the solid fraction.

In another embodiment the process of the invention is carried out as follows:
concentrating a composition comprising formic acid and levulinic acid to a vapor removal step to yield a concentrate and a vapor, and condensing said vapor to a condensate;
subjecting the concentrate to a solid-liquid separation to yield a solid fraction and a liquid fraction and recovering the liquid fraction;
subjecting the liquid fraction to solvent-solvent extraction by adding an organic solvent to yield an organic phase comprising levulinic acid and/or formic acid and an aqueous phase and recovering the organic phase; and
isolating the levulinic acid and/or the formic acid from the organic phase e.g. by distillation,
characterized in that the condensate and/or the aqueous phase is used to wash the solid fraction.

The concentrate can be subjected to a further vapor concentration step, for example a second concentration step, a third concentration step, etceteras.

Thus, the process of the invention can be carried out as follows:
subjecting a composition comprising formic acid and levulinic acid to a solid-liquid separation to yield a solid fraction and a liquid fraction and recovering the liquid fraction;
concentrating said liquid fraction by a first vapor removal step to yield a first concentrate and a first vapor, and condensing said first vapor to a first condensate;
subjecting the first concentrate to a further concentration step by vapor removal to yield a further concentrate and a further vapor, and condensing said further vapor to a further condensate;
subjecting the further concentrate to solvent-solvent extraction by adding an organic solvent to yield an organic phase comprising levulinic acid and/or formic acid and an aqueous phase and recovering the organic phase; and isolating the levulinic acid and/or the formic acid from the organic phase e.g. by distillation,
characterized in that the further condensate and/or the aqueous phase is used to wash the solid fraction.

Alternatively, the process of the invention can be carried out as follows:
- concentrating a composition comprising formic acid and levulinic acid to a first vapor removal step to yield a first concentrate and a first vapor, and condensing said first vapor to a first condensate;
- subjecting the first concentrate to a further concentration step by vapor removal to yield a further concentrate and a further vapor;
- subjecting the further concentrate to a solid-liquid separation to yield a solid fraction and a liquid fraction and recovering the liquid fraction;
- subjecting the liquid fraction to solvent-solvent extraction by adding an organic solvent to yield an organic phase comprising levulinic acid and/or formic acid and an aqueous phase and recovering the organic phase; and
- isolating the levulinic acid and/or the formic acid from the organic phase e.g. by distillation, characterized in that the further condensate and/or the aqueous phase is used to wash the solid fraction.

In the context of the invention, "a condensate" can refer to a single condensate, for example if the process comprises a single concentration step, or to a second, third condensate, etceteras, if the process comprises two or more concentration steps. The vapor of such concentration step(s) may be condensed e.g. by flashing, resulting in a condensate, and then used to wash the solid fraction. By washing of the solid fraction with condensate, any formic acid in the condensate is not be lost, but instead is retained.

The solid fraction that is washed in the process of the invention are obtained by a solid-liquid separation such as centrifugation or filtration. In the context of the invention, "solid fraction" and "the solids" are understood to be the same. skilled person knows how to conduct solid-liquid separation. Suitable methods are filtration and centrifugation. If filtration is used, e.g. using a filter plate, die, or filter cloth, the solids are typically in the form of a filter cake. If centrifugation is used, the solids are typically in the form of a pellet. In the context of the invention, "vapor condensate" and "condensate" are understood to be the same.

The inventor has surprisingly found that washing the solids with a condensate from a vapor results in higher yields of levulinic acid, as comparing to washing the solids with water. In the context of the invention, "water" is understood to be plain water and includes tap water and process water. It seems that a condensate is more efficient in recovering levulinic acid from solids than water. The state of the art is silent on this effect. For example, US2010/0312006 mentions the formation of char, but is silent on a washing solids. Formic acid is isolated by extraction. US2010/0324310 relates to the production of both formic acid and levulinic acid. In Example 3, the solid remaining at the end of the reaction is separated from the solution via vacuum filtration". US2010/0324310 is silent on recovering or washing of solids. U.S. Pat. No. 6,054,611 relates to the production of levulinic acid. It suggests that a cake be washed with water. U.S. Pat. No. 6,054,611 is silent on the isolation of formic acid and is silent on washing of solids with an aqueous phase or with a condensate, let alone that this would result in increased levulinic acid yields relative to washing with (plain) water. U.S. Pat. No. 8,138,371 refers to formic acid obtained as a condensate stream". However, this condensate is not used to wash the solids, nor is any suggestion made thereto.

The inventor also surprisingly found that washing with an aqueous phase results in a pellet or a filter cake which is less compressible, or less so, as compared to a filter cake or pellet which is obtained after washing with normal water.

The skilled person knows how to wash the solids with condensate or aqueous phase. For example, if the solids-liquid separation comprises filtration, the resulting filter cake can be washed by passing condensate and/or aqueous phase over the filter cake. If the solids-liquid separation comprises centrifugation, the resulting pellet can be washed by passing condensate and/or aqueous phase over said pellet. The pellet or filter cake can also be removed from the separation unit and be washed separately.

Washing of the solid fraction with condensate or with aqueous phase results in a washed solid fraction, and the remaining condensate or aqueous phase which is obtained after said washing is referred to as "the wash". If the solid-liquid separation comprises filtration, the wash is typically in the form of a filtrate. If the solid-liquid separation comprises centrifugation, the wash is typically in the form of a supernatant. The amount of condensate is not crucial. Already a little washing with condensate gives improved yield. One way to carry out washing is whilst monitoring the concentration of levulinic acid in the wash. When washing of the solids is started, the presence of levulinic acid in the wash indicates that, prior to the washing, the solid fraction comprises levulinic acid, and that this levulinic acid is recovered by the condensate. As the washing with the condensate proceeds, the concentration of the levulinic acid in the wash will decrease, until at a certain moment the concentration of levulinic acid in the wash remains more or less constant, preferably it approaches zero. Washing is preferably stopped when the concentration in the washe is more or less constant, or is or approaches zero. A constant concentration of levulinic acid in the wash may indicate presence of some levulinic acid in the vapor condensate, but preferably the condensate does not comprise any detectable amounts of levulinic acid. The skilled person can also determine the amount of formic acid in the filtrate.

It is possible to combine washing with condensate and water. For example, the process may be carried out such that the solids are washed first with water, then with condensate. Alternatively, the process may be carried out such that the solids are washed first with condensate, then with water. In both embodiments, the levulinic acid will be increased as compared to washing only with water. It is also possible to combine washing with aqueous phase and water. For example, the process may be carried out such that the solids are washed first with water, then with aqueous phase. Alternatively, the process may be carried out such that the solids are washed first with aqueous phase, then with water. In both embodiments, the filter cake will be less compressible as compared to washing only with water.

The process of the invention is particularly useful for operating in a continuous fashion. The condensate from the vapor concentration can simply be pumped to the solids using a pipe.

The composition comprising formic acid and levulinic acid may comprise a biomass hydrolysate. Preferably said biomass comprises lignocellulosic biomass. The biomass may be or may be derived from grass, cereal, starch, algae, tree bark, hay, straw, leaves, paper pulp, paper sludge, or dung. Paper pulp, or simply pulp, is a lignocellulosic fibrous material prepared by chemically or mechanically separating cellulose from wood, fibre crops or waste paper. Pulp is rich in cellulose and other carbohydrates. Paper sludge, or simply sludge, is a lignocellulosic fibrous containing cellulose fibres too short for usage in the paper industry. The biomass may comprise lignocellulosic biomass. Lignocellulosic biomass typically has a fibrous nature and comprises a bran fraction that contains the majority of lignocellulosic (bran) fibers. As an example, corn fiber is a heterogeneous complex of carbohydrate polymers and lignin. It is primarily composed of the outer kernel covering or seed pericarp, along with 10-25% adherent starch. Carbohydrate analyses of corn fiber vary considerably according to the source of the material. The lignocellulosic biomass may comprise hemicellulose.

In one embodiment, the composition is a biomass hydrolysate made by acid hydrolysis of lignocellulosic biomass.

In another embodiment, the composition is a made by acid hydrolysis of C6 sugars, particularly of fructose or glucose or mixtures thereof. Sucrose ($C_{12}H_{22}O_{11}$) can be broken down into one molecule of glucose ($C_6H_{12}O_6$) plus one molecule of fructose (also $C_6H_{12}O_6$, an isomer of glucose), in a weakly acidic environment by a process called inversion. Fructose can also be made by enzymatic isomerization of glucose. Sucrose is commonly produced from biomass such as beet, corn and cane.

A biomass hydrolysate may be obtained by acid hydrolysis of biomass. Suitable acids in the acid hydrolysis of biomass or C6 sugars include sulphuric acid, hydrochloric acid, and phosphoric acid. A preferred acid is sulphuric acid, preferably diluted sulphuric acid, for example at a concentration between 1.5-3%. The temperature in the acid hydrolysis may depend on the source of carbohydrates, and typically ranges between 120-250° C., preferably between 120-200° C. Said process may comprise one, two, or more stages. The pressure may also depend on the source of the biomass carbohydrates, as well as on the temperature, and may be anywhere between 1 and 50 bar, preferably between 5 and 40 bar, even more preferably between 10 and 30 bar. Suitable reactors include plugflow reactors, backmix reactors, and CSTR reactors. Different reactors for different stages may be used. The skilled person will understand that the reaction time for acid hydrolysis of biomass or C6 sugars depends on the reaction temperature, the pressure, as well as the source of biomass C6 sugars and the concentration of the acid. At higher reaction temperatures the reaction time may be shorter, whereas at lower reaction temperatures the reaction time may be longer. Likewise, at lower pressure, the reaction time may be longer whereas at higher pressure the reaction time may be shorter. The skilled person may therefore, without undue burden, establish suitable conditions with respect to temperature, reaction time, and pressure in order to obtain the biomass hydrolysate or C6 sugars acid hydrolysate. The reaction time may vary between one second and one day, preferably between 10 seconds and one hour.

The composition preferably comprises solids which are removed by solid-liquid separation. The solids may comprise organic material from biomass, or tar, which are preferably removed as they are undesired in the final product (levulinic acid or formic acid). The composition may comprise humins. A problem associated with the production levulinic acid and formic acid by acid hydrolysis of biomass or C6 sugars is formation of tar or humins, which can be produced in amounts up to 10 to 50% w/w of the total reaction mixture, creating a high overall purification and separation effort. Tar and char represent organic material which is insoluble in water, which is dark in colour and which tends to become viscous and very dark to almost black when concentrated. Tar can be formed during heating of organic material, for example by pyrolysis, but is also formed when carbohydrates are subjected to acid hydrolysis, particularly when done at high temperatures. Char usually refers to solid material, for example the remains of solid biomass that has been incompletely combusted, such as charcoal if wood is incompletely burned. Tar usually refers to (viscous) liquid, e.g. derived from the destructive distillation of organic matter. The presence of tar is undesired for a number of reasons. Firstly, its dark colour makes the product unattractive from the perspective of the user or customer. Secondly, the tar may negatively affect the performance of the bio-based product in the application. For this reason tar is preferably removed from the desired product. Yang and Sen (Chem. Sus. Chem. 2010, vol. 3, 597-603) report the formation of humins during production of fuels from carbohydrates such as fructose. They speculate that the humins are formed by acid-catalyzed dehydration. According to U.S. Pat. No. 7,896,944 the molecular weight of humins ranges from 2.5 to 300 kDa.

In the context of the invention, "extraction", "solvent extraction", and "solvent-solvent extraction" are understood to be the same. Extraction takes advantage of differences in the chemical properties of the feed components, such as differences in polarity and hydrophobic/hydrophilic character to separate them (T. C. Frank, L. Dahuron, B. S. Holden, W. D. Prince, A. F. Seibert, L. C. Wilson, Liquid-liquid extraction and other liquid-liquid operations and equipment in Perry's Chemical Engineering Handbook, 8th Edition, Section 15). Extraction yields an aqueous phase and an organic phase. The organic phase preferably comprises levulinic acid and formic acid and can be used to wash the solids obtained after solid-liquid separation. After the extraction the aqueous phase can be recovered to isolate levulinic acid from said aqueous phase, and optionally also formic acid. The aqueous phase can be recovered to wash the solid fraction. The skilled person knows how to recover the organic phase from the aqueous phase, e.g. by decanting.

In an embodiment, the organic solvent in the solvent-solvent extraction step comprises methyltetrahydrofuran (MTHF). The inventors have surprisingly found that using MTHF as a solvent in the solvent-solvent extraction may result in very good extraction efficiency for both formic acid and levulinic acid.

Washing with the condensate or with the aqueous phase may reduce water consumption as no or little external water is required. Moreover, the washed solid fraction has been found to contain less minerals and is therefore easier and less expensive to dispose of, than when the solids are not washed, or if they are washed with water. In addition, if the solids are washed with the aqueous phase, the filter cake becomes surprisingly dark in colour and less compressible than if the solids were not washed, or if they were washed with condensate or with plain water.

In a preferred embodiment, the process includes washing the solids with the condensate and with the aqueous phase, such that the solids are washed first with the aqueous phase and subsequently with the condensate. Washing with an organic phase and, and subsequently with a condensate has a synergistic effect. The inventor has found washing solids with the aqueous phase results in a washed solid fraction which is less compressible and much easier to wash, particularly when in the form of a filter cake, and when such washed solid fraction is subsequently washed with a condensate, the efficacy of the condensate to increase the levulinic acid yield is enhanced. In other words, the yield of levulinic acid after washing is further increased.

Washing with condensate and aqueous phase can be combined with washing with water. For example, the process may be carried out such that the solids are washed first with water, then with aqueous phase, then with condensate.

Alternatively, the process may be carried out such that the solids are washed first with aqueous phase, then with water, then with condensate. Alternatively, the process may be carried out such that the solids are washed first with aqueous phase, then with condensate, then with water. Alternatively, the process may be carried out such that the solids are washed first with aqueous phase, then with water, then with condensate, then with water. Alternatively, the process may be carried out such that the solids are washed first with water, then with aqueous phase, then with water, then with condensate, then with water. Multiple washing steps with condensate and aqueous phase is also possible. It is even possible to have a washing with condensate prior to washing with aqueous phase, but in this case it is preferred to have at least one washing with condensate after said washing with aqueous phase, as the synergistic effect described above, that is, the further increase of levulinic acid when washing with aqueous phase and condensate, is achieved when at least one washing of solids is done prior to at least one washing with condensate.

Washing with both condensate and aqueous phase also advantageously results in lower sulfur content in the washed solid fraction.

EXAMPLES

Example 1

100 g wood chips were impregnated for 90 minutes. After impregnation, the temperature was raised to the reaction temperature and the slurry was hydrolyzed in the presence of approximately 5 wt % hydrosulphuric acid without stirring. The resulting biomass hydrolysate suspension was subjected to solid/liquid separation. Results of the liquid fraction and the reaction conditions are stated in Table 2.

TABLE 2

| No | time in min | T in °C. | $H_2SO_4$ in wt %* | LA in wt % | FA in wt % | yield LA in % | yield FA in % |
|---|---|---|---|---|---|---|---|
| 1 | 90 | 170 | 4 | 3.952 | 1.940 | 42.4 | 51.4 |
| 2 | 240 | 160 | 4 | 4.396 | 2.041 | 46.3 | 53.1 |
| 3 | 180 | 170 | 2 | 4.298 | 2.037 | 47.7 | 53.6 |

*concentration on total mass (liquor + wood)

Example 2

The liquid fraction of the biomass hydrolysate of Example 1 can be cooled via evaporation resulting in a vapor. The resulting vapor can be condensed resulting in an aqueous solution (to give a condensate) comprising 0.8-1% formic acid, 0.02-0.4% acetic acid and 0-0.02% levulinic acid.

Comparative Example A 365 g of a biomass hydrolysate made according to Example 1 was filtered over a filter cloth with a pressure difference of 0.1 bar. The filter cake was washed three times with 50 g tap water at 25° C. The conductivity of the wash water, an indication for the ion content (organic acids and sulfuric acid) was measured to be 225.2 mS/cm in the first filtrate, 30.02 mS/cm in the first wash, 3.52 mS/cm in the second wash and 0.786 mS/cm in the third.

Comparative Example B 400 g of a biomass hydrolysate made according to Example 1 was filtered over a filter cloth with a pressure difference of 0.3 bar. The filter cake was washed five times with 76 g of tap water at 25° C. The concentration of levulinic acid, acetic acid and formic acid in the wash water are stated in Table 3. The washing efficiency is show in Table 4. The cake is dried after the washing and analyzed. The analysis data is found in Table 5.

Comparative Example C 400 g of a biomass hydrolysate made according to Example 1 was filtered over a filter cloth with a pressure difference of 0.3 bar. The filter cake was washed five times with 76 g of tap water at 60° C. The concentration of levulinic acid, acetic acid and formic acid in the wash water are stated in Table 3. The washing efficiency is show in Table 4. The cake is dried after the washing and analyzed. The cake is dried after the washing and analyzed. The analysis data is found in Table 5.

Example 3

401 g of a biomass hydrolysate made according to Example 1 was filtered over a filter cloth with a pressure difference of 0.3 bar. The filter cake was washed five times with 76 g of the condensate of Example 2. The concentration of levulinic acid, acetic acid and formic acid in the wash are stated in Table 3. The washing efficiency is show in Table 4. The cake is dried after the washing and analyzed. The cake is dried after the washing and analyzed. The analysis data is found in Table 5.

Example 4

403 g of a biomass hydrolysate made according to Example 1 was filtered over a filter cloth with a pressure difference of 0.3 bar. The filter cake was washed five times with 76 g of a solution described in Example 6, which is an aqueous phase obtain after extraction. The concentration of levulinic acid, acetic acid and formic acid in the wash water are stated in Table 3. The washing efficiency is show in Table 4. The cake is dried after the washing and analyzed. The cake is dried after the washing and analyzed. The analysis data is found in Table 5.

TABLE 3

| Wash | 1 | 2 | 3 | 4 | 5 | 1 | 2 | 3 | 4 | 5 |
|---|---|---|---|---|---|---|---|---|---|---|
| | Comparative Example B | | | | | Comparative Example C | | | | |
| Levulinic acid in wt % | 2.44 | 0.25 | 0.04 | 0 | 0 | 2.35 | 0.35 | 0.04 | 0 | 0 |
| Formic acid in wt % | 1.12 | 0.06 | 0 | 0 | 0 | | | | | |

TABLE 3-continued

| Wash | 1 | 2 | 3 | 4 | 5 | 1 | 2 | 3 | 4 | 5 |
|---|---|---|---|---|---|---|---|---|---|---|
| Acetic acid in wt % | 0.04 | 0 | 0 | 0 | 0 | | | | | |
| | | Example 3 (condensate) | | | | | Example 4 (aqueous phase) | | | |
| Levulinic acid in wt % | 2.42 | 0.15 | 0.02 | 0 | 0 | 2.30 | 0.74 | 0.63 | 0.61 | 0.57 |
| Formic acid in wt % | 1.14 | 0.79 | 0.80 | 0.79 | 0.80 | 1.02 | 0.35 | 0.31 | 0.31 | 0.31 |
| Acetic acid in wt % | 0.06 | 0.35 | 0.37 | 0.37 | 0.37 | 0.04 | 0.09 | 0.10 | 0.10 | 0.10 |

TABLE 4

| | Yield levulinic acid in % | | | | |
|---|---|---|---|---|---|
| Experiment | 1 | 2 | 3 | 4 | 5 |
| Comparative Example B | 97.9% | 99.7% | 100.0% | 100.0% | 100.0% |
| Comparative Example C | 97.1% | 99.7% | 100.0% | 100.0% | 100.0% |
| Example 3 | 98.8% | 99.9% | 100.0% | 100.0% | 100.0% |
| Example 4 | 97% | — | — | — | — |

From this experiment it is clear that washing the solids with a condensate form as vapor (Example 3) results in 1.7% higher yield of levulinic acid, as compared to washing the solids with tap water, as in comparative example B and C. On a large scale commercial plant, this is a very significant improvement.

TABLE 5

| Example | compressible | Elastic | Ca concentration (by XRF) |
|---|---|---|---|
| Comparative Example B | Yes | Yes | 0.05 |
| Comparative Example C | Yes | Yes | 0.02 |
| Example 3 | Yes | Yes | 0 |
| Example 4 | no | no | 0 |

From Table 5 it is clear that washing the solids with the aqueous phase obtained after extraction (Example 4) results in a filter cake which is not compressible and not elastic.

Example 5

A biomass hydrolysate according to Example 1 was enriched with pure levulinic acid to a levulinic acid concentration of 9.07 wt % with a formic acid concentration of 1.89 wt % to simulate the flash step in Example 2. 2.1 kg reaction solution was 5 times extracted 1.7 kg of fresh Methyltetrahydrofuran at 60° C. After the fifth extraction 99.1 of the levulinic acid and 98.8% of the formic acid present in the reaction solution could be collected in the organic layer.

Example 6

The extracted aqueous solution can be concentrated by the evaporation of water to yield a solution with concentration of levulinic acid of 0.6 wt %, of formic acid of 0.3 wt %, of acetic acid of 0.6 wt % and of sulfuric acid of 6.2 wt %.

The invention claimed is:

1. A process for isolating levulinic acid and formic acid from a composition comprising formic acid and levulinic acid, comprising:
   subjecting the composition to solid-liquid separation to produce a separated solid and a separated liquid;
   concentrating the separated liquid by vapor removal to produce a concentrate and a vapor;
   condensing the vapor to produce a condensate;
   subjecting the concentrate to solvent-solvent extraction to produce an aqueous phase and an organic phase;
   isolating a first fraction comprising levulinic acid, formic acid, or both levulinic acid and formic acid from the organic phase; and
   washing the separated solid with the aqueous phase to produce a washed solid and a wash liquid.

2. The process according to claim 1, wherein isolating the first fraction from the organic phase comprises distillation.

3. The process according to claim 1, wherein the composition is a biomass hydrolysate.

4. The process according to claim 3, wherein the biomass hydrolysate is made by acid hydrolysis of lignocellulosic biomass.

5. The process according to claim 1, wherein the composition is made by acid hydrolysis of fructose, glucose, or a combination thereof.

6. The process according to claim 1, wherein the separated solid is washed first with the aqueous phase, and thereafter with the condensate.

7. The process according to claim 1, further comprising washing the separated solid first with water and thereafter with the aqueous phase.

8. The process according to claim 1, wherein the wash liquid comprises a second fraction comprising levulinic acid, formic acid or both levulinic acid and formic acid; and wherein the process further comprises isolating the second fraction from the wash liquid.

9. The process according to claim 1, wherein the separated solid is washed until the wash liquid has no measurable quantity of levulinic acid or formic acid.

10. The process according to claim 1, wherein the condensate comprises 0.8 wt % to 1 wt % of formic acid, 0.02 wt % to 0.4 wt % of acetic acid, and up to 0.02 wt % of levulinic acid.

11. A process for isolating levulinic acid and formic acid from a composition comprising formic acid and levulinic acid, comprising:
   concentrating the composition by vapor removal to produce a concentrate and a vapor;
   condensing the vapor to produce a condensate;
   subjecting the concentrate to solid-liquid separation to produce a separated solid and a separated liquid;
   subjecting the separated liquid to solvent-solvent extraction with an organic solvent to produce an aqueous phase and an organic phase comprising levulinic acid, formic acid, or both levulinic acid and formic acid;
   isolating a first fraction comprising levulinic acid, formic acid, or both levulinic acid and formic acid from the organic phase;
   washing the separated solid with the aqueous phase to produce a washed solid and a wash liquid.

12. The process according to claim 11, wherein the composition is a biomass hydrolysate.

13. The process according to claim 11, wherein the composition is made by acid hydrolysis of fructose, glucose, or a combination of fructose and glucose thereof.

14. The process according to claim 11, wherein the separated solid is washed first with the aqueous phase, and thereafter with the condensate.

15. The process according to claim 11, further comprising washing the separated solid first with water and thereafter with the aqueous phase.

16. The process according to claim 11, wherein the wash liquid comprises a second fraction comprising levulinic acid, formic acid or both levulinic acid and formic acid; and wherein the process further comprises isolating the second fraction from the wash liquid.

17. The process according to claim 11, wherein the separated solid is washed until the wash liquid has no measurable quantity of levulinic acid or formic acid.

18. The process according to claim 11, wherein the condensate comprises 0.8 wt % to 1 wt % of formic acid, 0.02 wt % to 0.4 wt % of acetic acid, and up to 0.02 wt % of levulinic acid.

19. A process for isolating levulinic acid and formic acid from a composition comprising formic acid and levulinic acid, comprising:

separating the composition to produce a separated solid and a separated liquid;

concentrating the separated liquid by removing a vapor therefrom to produce a concentrate and the vapor;

condensing the vapor to produce a condensate;

separating the concentrate to produce an aqueous phase and an organic phase;

separating levulinic acid and formic acid from the organic phase; and washing the separated solid with the aqueous phase to produce a washed solid and a wash liquid.

20. The process of claim 19, wherein the composition is a biomass hydrolysate.

* * * * *